United States Patent [19]
Chantry et al.

[11] Patent Number: 5,985,589
[45] Date of Patent: Nov. 16, 1999

[54] LIPID KINASE

[75] Inventors: David H. Chantry, Seattle; Merl F. Hoekstra, Snohomish, both of Wash.; Douglas A. Holtzman, Cambridge, Mass.

[73] Assignee: ICOS Corporation, Bothell, Wash.

[21] Appl. No.: 09/225,951

[22] Filed: Jan. 6, 1999

Related U.S. Application Data

[63] Continuation of application No. 08/977,871, Nov. 25, 1997, Pat. No. 5,882,910, which is a continuation-in-part of application No. 08/777,405, Nov. 25, 1996, Pat. No. 5,858,753.

[51] Int. Cl.$^6$ .............................. C12Q 1/48; C12N 9/12; C12P 21/06; C07H 21/04
[52] U.S. Cl. ............................ 435/15; 435/194; 435/7.7; 435/69.1; 435/69.2; 435/252.3; 435/320.1; 530/350; 536/23.2; 536/23.5
[58] Field of Search .............................. 435/15, 194, 7.7, 435/69.1, 69.2, 252.3, 320.1; 530/350; 536/23.2, 23.5

[56] References Cited

U.S. PATENT DOCUMENTS

| | | | |
|---|---|---|---|
| 4,766,046 | 8/1988 | Abra et al. | 424/450 |
| 5,169,637 | 12/1992 | Lenk et al. | 424/450 |
| 5,180,713 | 1/1993 | Abra et al. | 514/31 |
| 5,185,154 | 2/1993 | Lasic et al. | 424/450 |
| 5,204,112 | 4/1993 | Hope et al. | 124/450 |
| 5,252,263 | 10/1993 | Hope et al. | 264/4.3 |
| 5,480,906 | 1/1996 | Creemer et al. | 514/453 |

FOREIGN PATENT DOCUMENTS

| | | |
|---|---|---|
| WO 92/02244 | 2/1992 | WIPO . |
| WO 96/25488 | 8/1996 | WIPO . |
| WO 97/46688 | 12/1997 | WIPO . |

OTHER PUBLICATIONS

Burgering and Coffer, "Protein Kinase B(c–Akt) in Phosphatidylinositol–3–OH Kinase Signal Transduction," *Nature*, 376:599–602 (1995).
Capecchi, M.R., "Altering the Genome by Homologous Recombination," *Science*, 244:1288–1292 (1989).
Eichholtz et al., "A Myristoylated Pseudosubstrate Peptide, a Novel Protein Kinase C Inhibitor," *J. Biol. Chem.*, 268:1982–1986 (1993).
Fraser et al., "Regulation of Interleukin–2 Gene Enhancer Activity by the T Cell Accessory Molecule CD28," *Science*, 251:313–316 (1991).
Godiska et al., "Chemokine Expression in Murine Experimental Allergic Encephalomyelitis," *J. Neuroimmun.*, 58:167–176 (1995).
Hiles et al., "Phosphatidylinositol 3–Kinase: Structure and Expression of the 110 kd Catalytic Subunit," *Cell*, 70:419–429 (1992).
Hu et al., "Cloning of a Novel, Ubiquitously Expressed Human Phosphatidylinositol 3–Kinase and Identification of its Binding Site on p85," *Mol. Cell. Biol.*, 13:7677–7688 (1993).

Hu et al., "Ras–Dependent Induction of Cellular Responses by Constitutively Active Phosphatidylinositol–3 Kinase," *Science*, 268:100–102 (1995).
Hunter, T., "When is a Lipid Kinase Not a Lipid Kinase? When it is a Protein Kinase," *Cell*, 83:1–4 (1995).
Kozak, M., "An Analysis of Vertebrate mRNA Sequences: Intimations of Translational Control," *J. Cell. Biol.*, 115:887–992 (1991).
Otsu et al., "Characterization of Two 85 kd Proteins that Associate with Receptor Tyrosine Kinases, Middle–T/pp60$^{c–src}$ Complexes, and PI3–Kinase," *Cell*, 65:91–104 (1991).
Pages et al., "Binding of Phosphatidyl–inositol–3–OH Kinase to CD28 is Required for T–cell Signalling," *Nature*, 369:327–329 (1994).
Panayotou and Waterfield, "Phosphatidyl–inositol 3–kinase: A Key Enzyme in Diverse Signalling Processes," *Trends in Cell Biol.*, 2:358–360 (1992).
Parker, P.J., "PI 3–kinase puts GTP on the Rac," *Current Biology*, 5:577–579 (1995).
Rameh et al., "Phosphatidylinositol (3,4,5)$P_3$ Interacts with SH2 Domains and Modulates PI 3–Kinase Association with Tyrosine–Phosphorylated Proteins," *Cell*, 83:821–830 (1995).
Rodriguez–Viciana et al., "Activation of Phosphoinositide 3–Kinase by Interaction with Ras and by Point Mutation," *EMBO Journal.*, 15:2442–2451 (1996).
Rudd, C.E., "Upstream–Downstream: CD28 Cosignaling Pathways and T Cell Function," *Immunity*, 4:527–534 (1996).
Sambrook et al., 9.47–9.51 in Molecular Cloning, Cold Spring Harbor Laboratory Press, Cold Spring Harbor, New York, (1989).
Stephens et al., "Characterization of a Phosphatidylinositol–Specific Phosphoinositide 3–kinase from Mammalian Cells," *Current Biology*, 4:203–214 (1994).
Stoyanov et al., "Cloning and Characterization of a G Protein–Activated Human Phosphoinositied–3 Kinase," *Science*, 269:690–693 (1995).
Thelan et al., "Wortmannin Binds Specifically to 1–phosphatidylinositol 3–kinase While Inhibiting Guanine Nucleotide–binding Protein–coupled Receptor Signaling in Neutrophil Leukocytes," *Proc. Natl. Acad. Sci. USA.*, 91:4960–4964 (1994).
Volinia et al., "Chromosomal Localization of Human p85α, a Subunit of Phosphatidylinositol 3–kinase, and its Homologous p85β," *Oncogene*, 7:789–793 (1992).

(List continued on next page.)

*Primary Examiner*—Ponnathapura Achutamurthy
*Assistant Examiner*—Tekchand Saidha
*Attorney, Agent, or Firm*—Marshall, O'Toole, Gerstein, Murray & Borun

[57] ABSTRACT

The present invention generally relates to a novel catalytic subunit of a lipid kinase designated p110δ. Polynucleotides encoding p110δ and recombinant p110δ polypeptides are provided along with antibodies to p110δ, assays for identifying inhibitors of p110δ, and the like.

5 Claims, 2 Drawing Sheets

OTHER PUBLICATIONS

Yao and Cooper, "Requirement for Phosphatidylinositol–Kinase in the Prevention of Apoptosis by Nerve Growth Factor," *Science,* 267:2003–2006 (1995).

Chantry, D. et al., "p110δ, a Novel Phosphatidylinositol 3–Kinase Catalytic Subunit That Associates with p85 and Is Expressed Predominantly in Leukocytes," *J. Biological Chemistry,* 272(31):19236–19241 (Aug. 1, 1997).

Genbank Accession No. U57843, "Human phosphatidylinositol 3–kinase delta catalytic subunit mRNA," deposited by Morris, A.J., dated May 10, 1997.

Vanhaesebroeck, B. et al., "p110δ, a novel phosphoinositide 3–kinase in leukocytes," *Proc. Natl. Acad. Sci., USA,* 94:4330–4335 (Apr. 1997).

Volinia, S. et al., "A human phosphatidylinositol 3–kinase complex related to the yeast Vps34p–Vps15p protein sorting system," *EMBO J.,* 14(14):3339–3348 (1995).

Hu, P. et al., "Cloning of a Novel, Ubiquitously Expressed Human Phosphatidylinositol 3–Kinase and Identification of Its Binding Site on p85," *Molecular and Cellular Biology,* 13(12):7677–7688 (1993).

Vanhaesebroeck et al. Faseb Journal (1996) vol. 10, No. 6, pp A 1395 (abstract only), Jun. 6, 1996.

```
p110 δ      -----------------------------YLE-ALSHLQSPLDPSTLLAEVCVEQCTFMDSRMKPLWIMYSNEEAGSGGSVG------IIFKNGDDLRQDMLT   67
p110 β      -----------------------------------------VILSELYVEKCKYMDSKMKPLWLVYNNKVFG-EDSVG------VIFKNGDDLRQDMLT   51
p110 γ      -----------------------------------------DPGLKAGALAIEKCKVMASKKKPLWLEFKCADPTALSNETIG----IIFKHGDDLRQDMLI   57
p110 α      -------------------------------RPDFMDALQGFLSPLNPAHQLGNLRLEECRIMSSAKRPLWLNWENPDIMSE--LLFQNNEIIFKNGDDLRQDMLT   73
p170/cpk    SGSTRQVVLQKSMERVQSFFLRNKCRLPLKPSLVAKELNIKSCSFFSSNAMPLKVTMVNADPLGEEINVMF----KVGEDLRQDMLA   83
Vps34       --------------------------------------------VLICDVCPETSKVFKSSLSPLKITF--KTTLNQ---PYH----LMFKVGDDLRQDQLV   49 p110 δ      LQMIQLMDVLWKQEGLDLRMTPYGCLPTGDRTGLIEVVLRSDTIANIQLNKSNMAATAAFNKDALLNWLKSKNPGEA-LDRAIEEFTLSC   156
p110 β      LQMLRLMDLLWKEAGLDLRMLPYGCLATGDRSGLIEVVSTSETIADIQLNSSNVAAAAAFNKDALLNWLKEYNSGDD-LDRAIEEFTLSC   140
p110 γ      LQILRIMESIWETESLDICLLPYGCISTGDKIGMIEIVDATTIAKIQ--QSTVGNTGAFKDEVLNHWLKEKSPTERKFQAAVERFVYSC   145
p110 α      LQIIRIMENIWQNQGLDLRMLPYGCLSIGDCVGLIEVVRNSHTIMQIQCK-GGLKGALQFNSHTLHQWLKD-KNKGEIYDAAIDLFTRSC   161
p170/cpk    LQMIKIMDKIWLKEGLDLRMVIFRCLSTGRDRGMVELVPASDTLRKIQVE-YGVTGS--FKDKPLAEWLRKYNPSEEEYEKASENFIYSC   170
Vps34       VQIISLMNELLKNENVDLKLTPYKILATGPQEGAIEFIP-NDTLASIL---SKYHGILGYLK--LH--YPDENATLGVQGWVLDNFVKSC   131 p110 δ      AGYCVATYVLGIGDRHSDNIMIRESGQLFHIDFGHFLGNFKTKFGINRERVPFILTYDFVHVIQQGKTNNSEK--FERFRGYCERAYTIL   244
p110 β      AGYCVASYVLGIGDRHSDNIMVKKTGQLFHIDFGHILGNFKSKFGIKRERVPFILTYDFIHVIQQGKTGNTEK--FGRFRQCCEDAYLIL   228
p110 γ      AGYCVATFVLGIGDRHNDNIMITETGNLFHIDFGHILGNYKSFLGINKERVPFVLTPDFLVMGTSGKKTSPH--FQKFQDICVKAYLAL   233
p110 α      AGYCVATFILGIGDRHNSNIMVKDDGQLFHIDFGHFLDHKKKKFGYKRERVPFVLTQDFLIVISKGAQECTKTREFERFQEMCYKAYLAI   251
p170/cpk    AGCCVATYVLGICDRHNDNIMLRSTGHMFHIDFGKFLGHAQMFGSFKRDRAPFVLTSDMAYVINGGEK--PTIR-FQLFVDLCCQAYNLI   257
Vps34       AGYCVITYILGVGDRHLDNLLVTPDGHFFHADFGYILGQDPKPF------PPLMKLPPQIIEAFGGAE---SSN--YDKFRSYCFVAYSIL   211 p110 δ      RRHGLLFLHLFALMRAAGLPEL--SCSKDIQYLKDSLALGKTEEEALKHFRVKFNEALRESWKTKVNWLAHNVSKDNRQ-   321
p110 β      RRHGNLFITLFALMLTAGLPEL--TSVKDIQYLKDSLALGKSEEEALKQFKQKFDEALRESWTTKVNWMAHTVRKDYRS-   306
p110 γ      RHHTNLLIIIFSMMLMTGMPQL--TSKEDIEYIRDALTVGKNEEDAKKYFLDQIEVWQRQRMDCAV-------   297
p110 α      RQHANLFINLFSMMLGSGMPEL--QSFDDIAYIRKTLALDKTEQEALFYFMKQMNDAHHGGWTTKQMDWIFHTIKQHALN-   329
p170/cpk    RKQTNLFLNLLSLMIPSGLPEL--TSIQDLKYVRDALQPQTTDAEATIFFTRLIESS-LGSIATKFNFFIHNLA------   328
Vps34       RRNAGLIINLFELMKTSNIPDIRIDPNGAILRVRERFNLNMSEEDATVHFQNLINDSVNALLPIVIDHL-HNLA-QYWRT   289
```

FIGURE 1

```
p110 δ    AKMCQFCEEAAARRQQLGWEAMLQYSFPLQLE--PSAQTWGPGTLRLPNRALL--VNVKFEGSEESFTFQVSTKDVPLALMACALRKKAT--VFRQPL--
p110 β    RKMRKFSEEKILSLVGLSWMDWLKQTYPPEHE--PSIPENLEDKL-YGGK-LI--VAVHFENCQDVFSFQVSPNMNPIKVNELAIQKRLT--IHGKED--
p110 γ    RGL---VTPRMAEVA  SRDPKLYAMHPWVTS--KPLPEYLWKKI-ANNCIFI--VIHRSTTSQTIKVSPDDTPGAILQSFFTKMAKKKS--LMDIPE--
p110 α    RNILNVCKEAVDLRDLNSPHSRAMYVYPPNVESSPELPKHIYNKLDKGQIIVIWVIVSPNNDKQKYTLKINHDCVPEQVIAEAIRKKTRSMLLSSEQLK

Consensus R........E........S....L....P...E--P..P......KL..........V.V............P......A..KK..........
                                                                                                    # p110 δ    ---VEQPEDYTLQVNGRHEYLYGNYPLCQFQYICSCLHSGLTPHLITMVHSSSILAMRDEQSNPAPQVQKPRAKPPPIPAKK
p110 β    ---EVSPYDYVLQVSGRVEYVFGDHPLIQFQYIRNCVMNRALPHFILVECCKIKKMYEQEMIAIEAAINR------------
p110 γ    ---SQSEQDFVLRVCGRDEYLVGETPIKNFQWVRHCLKNGEEIHVVLDTPPDPALDEVRKEEWPLVDDCT------------
p110 α    LCVLEYQGKYILKVCGCDEYFLEKYPLSQYKYIRSCIMLGRMPNLMLMAKESLYSQLPMDCFTMPSYS--------------

Consensus ......DY.L.V.GR.EY..G..PL.QFQYIR.C...G..PH..L............................
```

FIGURE 2

LIPID KINASE

This is a Continuation of U.S. application Ser. No. 08/977,871, filed Nov. 25, 1997, now U.S. Pat. No. 5,882,910, which in turn is a Continuation-in-Part of U.S. application Ser. No. 08/777,405, filed Nov. 25, 1996, now U.S. Pat. No. 5,858,753.

FIELD OF THE INVENTION

The present invention relates generally to the identification and isolation of a novel lipid kinase and more particularly to the discovery of a novel catalytic subunit related to phosphatidylinositol 3-kinase, herein designated p110δ.

BACKGROUND OF THE INVENTION

Phosphatidylinositol 3-kinase (PI 3-kinase) was originally identified as an activity associated with viral oncoproteins and growth factor receptor tyrosine kinases which phosphorylates phosphatidylinositol (PI) and phosphorylated derivatives of PI at the 3'-hydroxyl of the inositol ring [Panayotou et al., *Trends in Cell Biol.*, 2:358–360 (1992)]. The initial purification and molecular cloning of PI 3-kinase revealed that it was a heterodimer consisting of p85 and p110 subunits [Otsu et al., *Cell*, 65:91–104 (1992); Hiles et al., *Cell*, 70:419–429 (1992)].

The p85 subunit acts to localize PI 3-kinase to the plasma membrane by the interaction of its SH2 domain with phosphorylated tyrosine residues (present in an appropriate sequence context) in target proteins [Rameh et al. *Cell*, 83:821–830 (1995)]. Two isoforms of p85 have been identified, p85α which is ubiquitously expressed, and p85β, which is primarily found in brain and lymphoid tissues [Volinia et al., *Oncogene*, 7:789–793 (1992)].

The p110 subunit contains the catalytic domain of PI 3-kinase and three isofoniis (α, β and γ) of p110 have thus far been identified. p110α and β associate with p85 whereas p110γ which is activated by G protein βγ subunits, does not [Stoyanov et al., *Science*, 269:690–693 (1995)]. The cloning of p110γ revealed additional complexity within this family of enzymes. p110γ is closely related to p110α and β (45–48% identity in the catalytic domain), but does not make use of p85 as a targeting subunit, instead p110γ contains an additional domain termed a pleckstrin homology domain near its amino terminus. This domain allows interaction with the βγ subunits of heterotrimeric G proteins and it appears that it is this interaction that regulates its activity [Stoyanov et al., 1995]. Thus PI 3-kinases are defined by their amino acid identity or their activity. Additional members of this growing gene family include more distantly related lipid and protein kinases including Vps34, TOR1 and TOR2 of *Saccharomyces cerevisiae* (and their mammalian homologous such as FRAP and mTOR), the ataxia telangiectasia gene product, and the catalytic subunit of DNA dependent protein kinase. [See, generally, the review of Hunter, *Cell*, 83:1–4 (1995).]

The levels of phospliatidylinositol (3, 4, 5) triphosphate ($PIP_3$), the primary product of PI 3-kinase activation, increase upon treatment of cells with a wide variety of agonists. PI 3-kinase activation is therefore believed to be involved in a range of cellular responses including cell growth, differentiation and apoptosis [Parker et al., *Current Biology*, 5:577–579 (1995); Yao et al., *Science*, 267:2003–2005 (1995)]. The downstream targets of the phosphorylated lipids generated following PI 3-kinase activation have not been well characterized. In vitro, some isoforms of protein kinase C (PKC) are directly activated by $PIP_3$ and the PKC related protein kinase PKB has been shown to be activated by PI 3-kinase through an as-yet-undetermined mechanism [Burgering and Coffer, *Nature*, 376:599–602 (1995)].

PI 3-kinase also appears to be involved in a number of aspects of leukocyte activation. A p85 associated PI 3-kinase activity has been shown to physically associate with the cytoplasmic domain of CD28, an important co-stimulatory molecule for the activation of T cells in response to antigen [Pages et al., *Nature*, 369:327–329 (1994); Rudd, *Immunity*, 4:527–534 (1996)]. Activation of T cells through CD28 lowers the threshold for activation by antigen and increases the magnitude and duration of the proliferative response. These effects are linked to increases in the transcription of a number of genes including the T cell growth factor interleukin 2 (IL-2) [Fraser et al., *Science*, 251:313–316 (1992)]. Mutation of CD28 such that it can no longer interact with PI 3-kinase leads to a failure to initiate IL-2 production, suggesting a critical role for PI 3-kinase in T cell activation [Pages et al. 1994]. Based on studies using the PI 3-kinase inhibitor, wortmannin, there is evidence that PI 3-kinase(s) are also required for some aspects of leukocyte signalling through G protein-coupled receptors [Thelen et al., *Proc. Natl. Acad. Sci. USA.*, 91:4960–4964 (1994)].

There thus continues to exist a need in the art for further insights into the nature, function and distribution of PI 3-kinase providing means for effecting beneficial modulation of PI 3-kinase effects.

SUMMARY OF THE INVENTION

The present invention provides novel purified and isolated polynucleotides (i.e., DNA and RNA both sense and antisense strands) encoding a heretofore unknown catalytic member of the PI 3-kinase family, designated p110δ, which is expressed predominantly in leukocytes and thus likely plays a role in PI 3-Kinase mediated signaling in the immune system. Preferred DNA sequences of the invention include genomic and cDNA sequences as well as wholly or partially chemically synthesized DNA sequences. The DNA sequence encoding p110δ that is set out in SEQ ID NO: 1 and DNA sequences which hybridize to the noncoding strand thereof under standard stringent conditions (or which would hybridize but for the redundancy of the genetic code) are contemplated by the invention. Exemplary stringent hybridization conditions are as follows: hybridization at 65° C. in 3× SSC, 20 mM $NaPO_4$ pH 6.8 and washing at 65° C. in 0.2× SSC. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in Molecular Cloning, Cold Spring Harbor Laboratory Press, Cold Spring Harbor, N.Y. (1989). DNA/DNA hybridization procedures carried out with DNA sequences of the invention under stringent conditions are expected to allow the isolation of DNAs encoding allelic variants of p110δ; non-human species enzymes homologous to p110δ; and other structurally related proteins sharing one or more of the enzymatic activities, or abilities to interact with members or regulators, of the cell pathways in which p110δ participates.

Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating p110δ sequences and especially vectors wherein DNA encoding p110δ is operatively linked to an endogenous or exogenous expression control DNA sequence and a transcription terminator are also provided. The skilled worker will understand the various components of vectors [e.g. promoter(s), selectable marker(s), origin of replication(s), multiple cloning site(s), etc.], methods for manipulating vectors and the uses of vectors in transforming or transfecting host cells (prokaryotic and eukaryotic) and expressing p110δ of the present invention.

According to another aspect of the invention, procaryotic or eukaryotic host cells are stably or transiently transformed with DNA sequences of the invention in a manner allowing the expression of p110δ. Host cells expressing p110δ or p110δ along with a binding partner thereof can serve a variety of useful purposes. Such cells constitute a valuable source of immunogen for the development of antibody substances specifically immunore-active with p110δ. Host cells of the invention are also useful in methods for the large scale production of p110δ wherein the cells are grown in a suitable culture medium and the desired polypeptide products are isolated from the cells or from the medium in which the cells are grown by, for example, immunoaffinity purification.

As described herein, p110δ is a polypeptide which possess kinase catalytic activity.

In one aspect, the present invention provides p110δ polypeptides. The catalytic domain of p110δ polypeptide (amino acid residues 723–1044 of SEQ ID NO: 2) exhibits greater than 72% identity to the catalytic domain of p110β. Preferably, the polypeptides of this invention exhibit identity to the catalytic domain of p110β of 75% or greater. Even more preferably, the polypeptides comprise the amino acid residues according to SEQ ID NO: 2.

Yet another aspect of this invention provides polypeptide fragments or analogs of p110δ. The fragments of p110δ are useful in modulating the binding of p110δ and a binding partner (e.g., p85, Ras, and growth factor receptors). Analogs are polypeptides in which additions, substitutions, including conservative substitutions, or deletions of amino acid residues have been made in order to increase or decrease the binding affinity of the analog and a binding partner. These analogs of p110δ may be useful for modulating (i.e., blocking, inhibiting, or stimulating) the interaction between p110δ and a binding partner.

The polypeptides of this invention may be modified to facilitate passage into the cell, such as by conjugation to a lipid soluble moiety. For example, p110δ (or fragments or analogs thereof) may be conjugated to myristic acid. The peptides may be myristoylated by standard techniques as described in Eichholtz et al., *J. Biol. Chem.* 268:1982–1986 (1993), incorporated herein by reference. Alternatively, the peptides may be packaged in liposomes that may fuse with cell membranes and deliver the peptides into the cells. Encapsulation of the peptides in liposomes may also be performed by standard techniques as generally described in U.S. Pat. Nos. 4,766,046; 5,169,637; 5,180,713; 5,185,154; 5,204,112; and 5,252,263 and PCT Patent Application No. 92/02244, each of which is incorporated herein by reference.

Another aspect of this invention provides antibody substances (e.g., polyclonal and monoclonal antibodies, antibody fragments, single chain antibodies, chimeric antibodies, CDR-grafted antibodies, humanized antibodies and the like) specifically immunoreactive with p110δ. Antibody substances can be prepared by standard techniques using isolated naturally-occurring or recombinant p110δ. Specifically illustrating monoclonal antibodies of the present invention is the monoclonal antibody produced by hybridoma cell line 208F which was deposited with the American Type Culture Collection (ATCC), 12301 Parklawn Drive, Rockville, Md. 20852 on Oct. 8, 1996 and was assigned Accession No. HB 12200. The antibody substances are useful in modulating (i.e., blocking, inhibiting, or stimulating) the binding between p110δ and its binding partner. Antibody substances are also useful for purification of p110δ and are also useful for detecting and quantifying p110δ in biological samples by known immunological procedures. In addition, cell lines (e.g., hybridomas) or cell lines transformed with recombinant expression constructs which produce antibody substances of the invention are contemplated.

In another aspect, methods of identifying a modulator that inhibits or activates the kinase activity of p110δ are contemplated. In a preferred method, kinase activity of p110δ in the presence and absence of a potential modulator compound is determined and compared. A reduction in the kinase activity observed in the presence of the test compound indicates that the test compound is an inhibitor. An increase in the kinase activity observed in the presence of the test compound indicates that the test compound is an activator.

In another aspect, this invention provides methods of identifying a modulator that affects the binding of p110δ and a binding partner (e.g., p85, Ras and growth factor receptors) and thereby increases or decreases the effective specific subcellular concentration of p110δ. In this method, p110δ and its binding partner are incubated in the presence and absence of a putative modulator under conditions suitable for binding. The observed binding in the presence and absence of the modulator compound is compared. A reduction in the observed binding indicates that the compound inhibits binding. An increase in the observed binding indicates that the compound increases binding. These modulators are useful in affecting localization of p110δ to a specific subcellular location.

Modulators contemplated by the invention, for example, include polypeptides, polypeptide fragments of p110δ, and other organic and inorganic chemical compounds.

This invention further provides a method of detecting the presence of p110δ in a biological sample. The method comprises exposing a p110δ specific antibody to a biological sample to be tested. The binding of the p110δ specific antibody to p110δ in the biological sample is detected by well-known means. For example, a second antibody conjugated to horseradish peroxidase (HRP) that specifically recognizes anti-p110δ antibody is used to detect anti-p110δ antibody. A positive color reaction catalyzed by HRP indicates that p110δ is present in the biological sample.

Yet another aspect of this invention provides a diagnostic reagent for detecting the presence of polynucleotides that encode p110δ in biological samples. The diagnostic reagent is a detectably labeled polynucleotide encoding part or all of the amino acid residues of p110δ set out in SEQ ID NO: 2. The presence of the polynucleotide in the biological sample is determined by hybridization of the diagnostic reagent to the polynucleotide encoding p110δ. Exemplary biological samples include chromosomes and chromosomal DNA. The diagnostic reagent is detectably labeled with well-known labels, including radioactive, enzymatic or other ligands, such as avidin/biotin, and fluorescent tags which are capable of providing a detectable signal.

The DNA sequence information provided by the present invention also makes possible the development, by homologous recombination or "knockout" strategies [see e.g. Capecchi, *Science* 244:1288–1292 (1989)] of mammals that fail to express a functional p110δ or that express a variant analog of p110δ. The mammals of the present invention comprise a disrupted p110δ gene or a disrupted homolog of the p110δ gene. The general strategy utilized to produce the mammals of the present invention involves the preparation of a targeting construct comprising DNA sequences homologous to the endogenous gene to be disrupted. The targeting construct is then introduced into embryonic stem cells (ES cells) whereby it integrates into and disrupts the endogenous gene or homolog thereof. After selecting cells which include the desired disruption, the selected ES cells are implanted into an embryo at the blastocyst stage. Exemplary mammals include rabbits and rodent species.

Polynucleotides of the invention are also expected to be useful in chromosomal localization studies potentially useful in detection of inappropriate and/or over expression of p110δ in abnormal cell types.

Also made available by the invention are antisense polynucleotides relevant to regulating expression of p110δ by those cells which ordinarily express the same.

Numerous additional aspects and advantages of the present invention will be apparent from the following detailed description of illustrative embodiments thereof.

BRIEF DESCRIPTION OF THE DRAWINGS

FIG. 1 presents an alignment of the predicted catalytic domain of p110δ with the corresponding domain of other members of the PI 3-kinase family. The alignment was performed using Geneworks (Intelligenetics, Inc., Mountain View, Calif.).

FIG. 2 presents an alignment of the predicted Ras regulatory region of p110δ with the corresponding region of other members of the PI 3-kinase family. The conserved lysine which is essential for interaction with Ras is indicated by the symbol # below the consensus line.

DETAILED DESCRIPTION OF THE INVENTION

The present invention is illustrated by the following examples. Example 1 describes the cloning and characterization of cDNA encoding p110δ. p110δ was obtained by combining three separate cDNA clones spanning the full length p110δ cDNA. Example 2 describes the expression and kinase activity of recombinant p110δ. Example 3 describes the isolation of a mouse genomic p110δ clone. Baculovirus expression of p110δ is described in Example 4. Example 5 assesses the ability of recombinant p110δ to associate with p85 in transfected mammalian cells. The expression of p110δ in various human tissues is disclosed in Example 6. Example 7 provides monoclonal antibodies specific for p110δ. Example 8 describes experiments directed to chromosomal localization of p110δ. Example 9 describes experiments related to the association of p110δ and growth factor receptors. Example 10 discusses the use of transgenic animals which are engineered to include a disruption in the p110δ gene.

EXAMPLE 1

Degenerate oligonucleotide primers were designed for use in a PCR reaction based on sequences conserved in the catalytic domain of known PI 3-kinases. The sense primer was GCAGAC<u>GGATCC</u>GGIGAYGAYHKIAGRCARGA (SEQ ID NO: 3) encoding the sequence GDDLRQD (SEQ ID NO: 4), and the anti-sense primer was GCAGAC<u>GAATTC</u>RWRIC-CRAARTCIRYRTG (SEQ ID NO: 5) encoding the amino acid sequence HIDFGH (SEQ ID NO: 6). Bam HI and Eco RI restriction sites are underlined. PCR reactions consisted of 100 ng of cDNA template [from human peripheral blood mononuclear cells (PBMC) activated for 18 hours with 10 ng/ml phorbol myristate and 250 ng/ml calcium ionophore (Sigma)], 10 μg/ml oligonucleotide primers, 50 mM KCl, 10 mM Tris HCl (pH 8.4), 1.5 mM MgCl$_2$, 200 mM dNTPs, and 1U of Taq polymerase in a final volume of 100 μl. Reactions were performed using denaturation for 1 minute at 94° C., annealing at 60° C. for 2 minutes and extension for at 72° C. for 1 minutes for 3 cycles. The procedure was then repeated using 56° C. annealing temperature for 3 cycles, 52° C. annealing temperature for 3 cycles and 50° C. annealing temperature for 30 cycles. Amplified products were gel purified, digested with Bam HI and Eco RI, and subcloned into the vector pBSSKII+ (Stratagene, La Jolla, Calif.) for sequencing. All DNA for sequencing was prepared using the Wizard Miniprep DNA Purification System (Promega, Madison, Wis.). Sequencing was performed on the Applied Biosystems Model 373 automated sequencer. Data bank searches were made using the BLAST program, and protein and DNA alignments were made using the Geneworks program (Intelligenetics Inc. Mountain View Calif.) One clone contained a 399 bp insert that encoded a 133 amino acid open reading frame showing similarity to p110β. This clone was a partial clone of a new catalytic subunit of PI 3-kinase designated p110δ.

To identify a cDNA encoding p110δ, specific oligonucleotide primers were designed based on the sequence of the 399 bp PCR product. The forward primer was CATGCTGAC-CCTGCAGATGAT (SEQ ID NO: 7) and the reverse printer was AACAGCTGCCCACTCTCTCGG (SEQ ID NO: 8). These primers were used to screen a cDNA library from human PBMC stimulated with PMA and ionomycin (as described above) in the mammalian expression vector pRc-CMV. Successive rounds of PCR were performed initially on pools of 100,000 clones and subsequently on smaller pools until a single clone termed PBMC #249 was isolated by colony hybridization using the PCR product labelled by random priming as a probe. This cDNA was not full length. Therefore to identify longer cDNA clones the same approach was used to screen a cDNA library from human macrophages (also in the vector pRcCMV). This led to the isolation of an additional cDNA clone (M#928) which extended the cDNA sequence by 1302 bp.

The remaining 5' end of the cDNA encoding p110δ was obtained by 5' RACE PCR (Clonetech, Palo Alto, Calif.) Two anti-sense gene-specific oligonucleotide primers were designed based on the 5' end of cDNA M#928 for RACE PCR reactions. The primary RACE primer was GGGCCACAT-GTAGAGGCAGCGTTCCC (SEQ ID NO: 9) and the nested RACE primer was GGCCCAGGCAATGGGGCAGTCCGCC (SEQ ID NO: 10). Marathon-Race reactions were set up using Marathon-ready cDNA template from Human Leukocytes and the Advantage Core PCR Reaction kit (Clonetech, Palo Alto, Calif.) following the manufacturer's protocol. Touchdown PCR cycling conditions were modified to improve the specificity of the Marathon-RACE PCR primary reaction as follows: denaturation at 94° C. for 2 minutes, followed by 5 cycles of denaturation at 94° C. for 30 seconds and annealing and extension at 72° C. for 3 minutes; 5 cycles of denaturation at 94° C. for 30 seconds and annealing and extension at 70° C. for 3 minutes; and 25 cycles of denaturation at 94° C. for 30 seconds and annealing and extension at 68° C. for 3 minutes.

Amplified products were used as templates in a nested PCR reaction using the previously described cycling parameters. The reamplified products were then analyzed by Southern blotting using oligonucleotide probes specific for p110δ. Probes (100 ng each) were end-labelled with $^{32}$P-γATP, and hybridized and washed under standard conditions (Frisch and Sambrook). The sequences of the two probes were GATGCGGAACGGCTGCTCCAGGG (SEQ ID NO: 11) and CCAGGGACCACAGGGACACAGAG (SEQ ID NO: 12).

The specific 5' RACE PCR products identified in this manner were gel purified and subcloned into the TA vector PCRII (Invitrogen, San Diego, Calif.) according to the manufacturer's instructions. Three independent clones were sequenced to ensure the veracity of the 5' sequence.

A full length cDNA for p110δ was assembled from clones #249, M#928 and the 5' RACE PCR products. The 5' RACE product was used as a template in PCR using the 5' primer AGTTACG<u>GATCC</u>GGCACCATG(GACTACAAGGACGACGATGACAAG)CCCCCTGGGGTGGA CTGCCC (SEQ ID NO: 13) and the 3' primer CCACATGTA-GAGGCAGCGTTCC (SEQ ID NO: 14). The 5' primer includes a Bam HI site (underlined), and sequences that encode the FLAG peptide sequence DYKDDDDK (SEQ ID NO: 15) (shown in parenthesis) which is recognized by the M2 anti-FLAG monoclonal antibody (Kodak Scientific Imaging Systems, New Haven, Conn.). The resulting PCR product was digested with Bam HI and Afl II, and was ligated along with an Afl II/Pvu I fragment derived from the clone M#928 and a Pvu II/Xba I fragment derived from PBMC clone #249 into the Bam HI/Xba I sites of the mammalian expression vector pcDNA3 (Invitrogen, San Diego, Calif.). The vector containing the FLAG-tagged composite p110δ cDNA is designated pCDNA3:p110δFLAG. In the FLAG-tagged p110δ, the FLAG-tag is located immediately after the initiating methionine.

A full-length composite cDNA encoding p110δ is shown in SEQ ID NO: 1. The sequence of p110δ includes an open reading frame of 3135 nucleotides which is predicted to encode a protein of approximately 114 KD. In addition, there are 197 bp of 5' and 1894 bp of 3' untranslated sequence. The sequence around the predicted initiating methionine is in good agreement with that required for optimal translational initiation [Kozak, M., *J. Cell Biol.*, 115:887–992 (1991)] and the presence of stop codons in the 5' untranslated sequence is consistent with the isolation of the complete coding region of p110δ.

Comparison of the deduced amino acid sequence of p110δ (SEQ ID NO: 2) with other PI 3-kinases reveals that it is most closely related to p110β. Similar to p110β, the catalytic domain of p110δ is found in the C-terminus of the protein and is believed to be reside within amino acid residues 723–1044 of SEQ ID NO: 2. An alignment of the predicted carboxyl terminal catalytic domains of the PI 3-kinase family (including p110δ residues 723 through 1044 of SEQ ID NO: 2) is shown in FIG. 1. Table 1 shows the identity of p110δ to other members of the PI 3-kinase family. p110δ is 72% identical to p110β in this region but is less closely related to p110α (49%) and p110γ (45%). Table 1 also shows that p110δ shows low identity to cpk/p170 and the yeast Vps 34 protein, 31 and 32% respectively.

TABLE 1

|        | p110δ | p110β | p110α | p110γ | cpk/p170 | Vps34 |
|--------|-------|-------|-------|-------|----------|-------|
| p110δ  | —     | 72    | 49    | 45    | 31       | 32    |
| p110β  |       | —     | 49    | 48    | 37       | 31    |
| p110α  |       |       | —     | 45    | 39       | 29    |
| p110γ  |       |       |       | —     | 39       | 31    |

TABLE 1-continued

|         | p110δ | p110β | p110α | p110γ | cpk/p170 | Vps34 |
|---------|-------|-------|-------|-------|----------|-------|
| cpk/p170 |      |       |       |       | —        | 28    |
| Vps34   |       |       |       |       |          | —     |

Dendrogram analysis revealed that p110β and p110δ form a distinct sub-branch of the PI 3-kinase family. The distantly related ATM gene and the catalytic subunit of DNA dependent protein kinase have been included for comparison.

It has been demonstrated that PI 3-kinase is an important intermediate in the Ras pathway [Hu et al. 1993; Rodriguez-Viciana et al., EMBO Journal, 15:2442–2451 (1996)]. A constitutively active form of PI 3-kinase has been shown to increase transcription of the c-fos gene, activate the protein kinase Raf, and stimulate oocyte maturation [Hu et al., 1995]. The effects of PI 3-kinase in these systems can be blocked by co-expression of a dominant negative form of Ras indicating that PI 3-kinase acts upstream of Ras. Additional studies have shown that Ras can physically interact with PI 3-kinase in vitro and stimulate its kinase activity [Rodriguez-Viciana et al., 1996]. Thus PI 3-kinase can either act as an effector of Ras-dependent signalling or be directly activated by interaction with Ras. A specific region at the amino terminus of the p110 subunits termed the Ras regulatory domain is responsible for this interaction [Rodriguez-Viciana et al. 1996]. Comparison of the sequence of p110δ with other p110 subunits indicates that this region is also conserved in p110δ including a lysine residue which has been shown to be essential for physical association with Ras (Rodriguez-Viciana et al., 1996). Thus p110δ is also likely to interact with the Ras pathway. FIG. 2 presents an alignment of the proposed Ras binding sites of four p110 subunits including p110δ residues 141 through 310 of SEQ ID NO: 2.

EXAMPLE 2

The FLAG-tagged p110δ was expressed by transfecting pCDNA3:p110δFLAG into COS cells using DEAE dextran. Three days after transfection, expression of p110δ was determined by immunoprecipitations and western blotting using the M2 monoclonal antibody (Kodak Scientific Imaging Systems) according to the manufacturer's instructions. PI 3-kinase activity was determined as described [Hu et al., *Mol. Cell. Biol.*, 13:7677–7688 (1993)].

To determine the PI 3-kinase activity of p110δ, 5μl of immunoprecipitated p110δ was mixed with 1 μl of PI/EGTA and incubated at room temperature for 10 minutes [PI/EGTA is 10 mg/ml PI(Sigma) in CHCl$_3$, which has been dried under a vacuum, resuspended in 20 mg/ml DMSO in the presence or absence of various concentrations of the PI3 kinase inhibitor wortmannin and diluted 1:10 in 5 mM EGTA] and added to 1 μl 10× HM buffer (200 mM HEPES pH7.2, 50 mM MnCl$_2$), 0.5 μl γ$^{32}$PATP (10 mCi/ml-300 Ci/mmol), 1 μl 100 μM ATP, and 1.5 μl H$_2$O and incubated at 30° C. for 15 minutes. The reactions were terminated by addition of 100μl 1M HCl. Lipids were extracted with 200 μl CHCl$_3$/MeOH (1:1) by vortexing for 1 minute followed by centrifugation at 16,000×g for 2 minutes at room temperature. The lipids were further extracted with 80 μl 1M HCl/MeOH (1:1) by vortexing for 1 minutes, followed by centrifugation at 16,000×g for 2 minutes at room temperature. The lipids were dried under vacuum, resuspended in 10 μl CHCl$_3$/MeOH (1:1) and spotted 2 cm from the bottom of a dry Silica gel 60 chromatography plate (VWR) that had been pre-impregnated with 1% $K_2C_2O_4$ in $H_2O$. 250 μg of crude phosphoinositides (Sigma) were spotted as markers. The products were resolved by chromatography for 2 hours in $CHCl_3$/MeOH/4N $NH_4OH$ (9:7:2), allowed to dry and placed in an Iodine vapor tank for 5 minutes in order to visualize the crude standards. The position of the standards was marked with a pencil and the plate was autoradiographed.

Phosphorylated lipids were generated in the kinase assays. The major product was phosphatidyl inositol phosphate (PIP). Furthermore, the generation of these phosphorylated lipids was inhibited in a dose dependent manner by wortmannin (approximately 50% of the activity was inhibited at 100 nM wortmannin) demonstrating that p110δ is a functional PI3 kinase.

EXAMPLE 3

A mouse genomic clone encoding p110δ was isolated as described below. A mouse 129 SvEv lambda genomic library (Stratagene, La Jolla, Calif.) was screened using a fragment of the human cDNA clone for p110δ (corresponding to amino acids 739 to 1044 of SEQ ID NO.: 2) labelled to high specific activity (~1×10$^9$ dpm/ug DNA) by random priming using the Random Primed DNA labelling Kit (Boehringer Mannheim). Hybridization was performed for sixteen hours at 42° C. in buffer containing 50% formamide, 5× SSC, 5× Denhardts, 0.05M Na phosphate, and 100 ug/ml salmon sperm DNA. Filters were washed in 0.2× SSC/0.1% SDS at 50° C. A single clone was isolated. Purified phage DNA was digested with Not I and inserts were subcloned into the vector pBSSKII+ (Stratagene, La Jolla, Calif.) for sequencing. This clone was approximately 16 kb and included the entire catalytic region of p110δ.

EXAMPLE 4

Recombinant p110δ may be expressed in SF9 insect cells using a baculovirus expression system.

As discussed in Example 1, FLAG-tagged p110δ encoding sequences are useful in expressing the kinases of this invention. Upon expression in insect cells, a monoclonal antibody that recognizes the FLAG tag (Eastman Kodak, Rochester, N.Y.) is used to purify large quantities of the FLAG-PIK-related kinase fusion protein. Infected insect cells are incubated for 48 hours and lysed in lysis buffer (25 mM 2-glycerolphosphate, 50 mM sodium phosphate pH 7.2, 0.5% Triton-X 100, 2 mM EDTA, 2 mM EGTA, 25 mM sodium fluoride, 100 μM sodium vanadate, 1 mM PMSF, 1 μg/ml leupeptin, 1 μg/ml pepstatin, 1 mM benzamidine, and 2 mM DTT). Expressed FLAG fusion proteins are purified over a column containing anti-FLAG antibody M2 affinity resin (Eastman Kodak). The column is washed with 20 column volumes of lysis buffer, then 5 column volumes of 0.5M lithium chloride, 50 mM Tris pH 7.6, 1 mM DTT, and then eluted either with 0.1M glycine pH 3.0 followed by immediate neutralization or by competitive elution with the FLAG peptide. For histidine tagged proteins, Ni-NTA agarose (Qiagen) is used for protein purification.

Plasmids for expression of p85 and p110δ in the baculovirus expression system were prepared as follows.

The plasmid pcDNA3:p85 DNA as described in Example 5 was digested with BamHI and EcoRI and the 2.5 kb FLAG-p85 band containing the entire p85 coding region with the FLAG tag was gel purified and inserted in BamHI-EcoRI site of pFastbac Dual (Gibco BRL). The ligation mixture was transformed into E. coli XL-1 blue (Stratagene) and plated on ampicillin containing plate. A clone was purified that carries the pFastbac-Dual-p85 plasmid.

The pFastbac-Dual-p85 plasmid was transformed into E. coli DH10 Bac cells and white colonies were selected on plates containing kanomycin, gentamycin, tetracyoline, X-gel and IPTG. One white colony was restreaked on a similar plate for repurification. Recombinant p85-bacmid DNA was purified from this clone.

The plasmid pcDNA3:p110δ containing the entire p110δ coding region with the FLAG tag was digested with BamHI and XbaI, gel purified and inserted into the BamHI-XbaI site of pFastbac HTb (Gibco BRL) such that the coding region of FLAG-tagged p110δ was in frame with the coding sequences of the histidine-tag present in the vector. The ligation mixture was then transformed into E. coli XL-1 blue (Stratagene). A clone carrying pFast-bac Htb p110δ was isolated and the plasmid DNA was isolated and the plasmid DNA was purified. P110δ-bacmid DNA was prepared by transforming E. coli DH10 bac cells as described for p85-bacmid.

To prepare virus stocks, the p85-bacmid and the p1106δ-bacmid DNAs were separately transfected into SF-9 cells according to the Gibco BRL suggested protocol. Forty-eight hours after transfection, the SF9 cell pellet and baculovirus produced by the transfected cells were harvested. The virus was stored at 4° C. in Grace's Complete media containing 10% FBS, pennicillin-streptomycin, and gentamicin. This viral prep was used to make a high titer (P2) virus stock. The P2 virus stock was used to infect a 50 ml culture of SF9 cells. The cells were collected 48 hours after infection and centrifuged at low speed to pellet the cells without lysis. The cell pellet was stored at −20° C. for 24 hours before lysis. The cells were lysed in 5 ml of lysis buffer (50 mM Tris, pH 8.0; 500 mM NaCl; 1% NP40; 100 μm PMSF). Expression of p85 and p110δ was confirmed by immunoblot using the M2 antibody anti-FLAG as a probe. The SF-9 transfected cells produced an approximately 85 kDa protein and a 110 kDa protein which were immunoreactive with anti-FLAG antibodies.

The P2 virus stock were also used to co-infect a 2 liter culture of SF9 cells. The cells were collected 48 hours after infection, centrifuged at low speed to pellet the cells without lysis and stored at −20° C. A cell pellet from 150 mls of this culture was lysed in 7.5 ml of lysis buffer (50 mM $NaPO_4$ pH7.2; 0.5% NP-40; 10 mM imidazole, 25 mM NaF, 100 μM $Na_3VO_4$; 0.5 mM AEBSF; 1 μg/ml leupeptin; 1 μg/ml pepstatin A) and incubated on ice for 15 minutes. The lysate was then centrifuged for 30 minutes at 10,000×g. The supernatant was removed and any DNA in the lysate resulting from broken nuclei was sheared by aspirating through an 20 gauge needle. Particulate matter was then removed by filtering through a 0.8 micron filter followed by a 0.2 micron filter. This cleared lysate was adjusted to contain 5 mM β-mercaptoethanol and 0.4 M NaCl. A 1 ml Ni-NTA-agarose column (Qiagen) was equilibrated in Buffer A (0.4 M NaCl; 5 mM β-mercaptoethanol; 0.1% Triton X-100; 50 mM $NaPO_4$ 10 mM imidazole; 25 mM NaF, 100 μM $Na_3VO_4$; 0.5 mM AEBSF; 1 μg/ml leupeptin; 1 μg/ml pepstatin A) prior to loading the cleared lysate. The sample was loaded at a flow rate of 0.25 ml/minute, washed 5 ml of Buffer A and then eluted in 10 ml of a gradient of 50 to 500 mM imidazole in Buffer A.

EXAMPLE 5

The ability of p110δ to associate with p85 was assessed by Western blot analysis. COS cells were transiently transfected with p110δ (see Example 2) and association with endogenous p85 was determined by coimmunoprecipitation. As controls, cells were also transfected with FLAG-tagged p85 DNA or empty vector. The cDNA encoding the p85 subunit was isolated from human leukocyte cDNA by Marathon-race PCR. The cDNA sequence of p85 was described in Otsu, *Cell*, 65:91–104 (1992). The p85 cDNA was modified for expression as a FLAG-tagged protein (pcDNA3:p85) in a manner similar to the protocols described herein for p110δ.

COS cells were lysed in 3 ml Buffer R (1% Triton X-100, 150 mM NaCl, 10 mM Tris pH7.5, 1 mM EGTA, 0.5% NP-40, 0.2mM $Na_3VO_4$, 0.2 mM PMSF, 1× aprotinin, 1× leupeptin, 1× pepstatin A). After 10 minutes at 4° C., the lysates were sheared by passing through a 27G needle several times. The lysates were clarified by centrifugation at 16,000×g for 10 minutes at 4° C., and immunoprecipitated for 2 hours at 4° C. with either 1 μg anti-p110β (Santa Cruz Laboratories, Santa Cruz, Calif.), 10 μg anti-FLAG-M2 (Eastman Kodak), or 1 μg anti-p85 (Santa Cruz Laboratories). Immune complexes were bound to 60 μl of Protein G-sepharose (Pharmacia) for 30 minutes at 4° C. then washed 3 times in 300 μl of Buffer R and resuspended in 25 μl PAN (100 mM NaCl, 10 mM PIPES pH7.0, 20 μg/ml Aprotinin). 5 μl of each immunoprecipitate was resolved by 8% SDS-PAGE (Novex), transferred to Immobilon-P (Millipore), blocked one hour at room temperature in 5% non-fat dried milk in TBS, and detected by Western blotting using either anti-p85 rabbit polyclonal antibodies (Santa Cruz Laboratories) at 1 μg/ml followed by goat anti-rabbit IgG HRP conjugated secondary antibody (Boehringer) or anti-FLAG-M2 monoclonal antibody at 10 μg/ml followed by goat anti-mouse IgG HRP conjugated secondary antibody (Boehringer).

The Westerns showed that anti-FLAG-M2 antibody recognized immune complexes including FLAG-tagged p85 and FLAG-tagged p110δ.

EXAMPLE 6

While the activation of PI 3-kinase in a wide range of biological systems has been extensively studied, less is known concerning the cell type specific expression of particular p110 isoformis. The expression of p110δ in human heart, brain, placenta, lung, liver, skeletal muscle, kidney, pancreas, spleen, thymus, prostate, testis, uterus, small intestine, colon, and PBMC was determined by Northern blot analysis.

$^{32}$P-labelled cDNA probes were prepared by PCR using 10 ng of plasmid DNA template encoding p110δ, as described previously [Godiska et al, *J. Neuroimmun.*, 58:167–176 (1995)]. The forward primer was CTGCCATGT-TGCTCTTGTTGA (SEQ ID NO: 16) and the reverse primer was GAGTTCGACATCAACATC (SEQ ID NO: 17). Reactions were heated for 4 minutes at 94° C., followed by 15 cycles of denaturation for 1 minutes at 94° C., annealing for 1 minutes at 55° C. and extension for 2 minutes at 72° C.

Unincorporated nucleotides were removed by passing the reaction over a sephadex G50 column (Boehringer Mannheim Biochemicals). A Multiple Tissue Northern blot (Clontech, Palo Alto, Calif.) was probed and washed under stringent conditions according to the manufacturer's recommendations. The autoradiograph was exposed for 1–4 days at −80° C. with intensifying screens.

Northern blot analysis revealed a single transcript of approximately 5.4 kb (consistent with the size of the composite cDNA). The highest levels of expression were seen in peripheral blood mononuclear cells (PBMC) and in spleen and thymus. On prolonged exposure of the autoradiograph, expression of p110δ could also be detected in testes, uterus, colon, and small intestine, but not in other tissues examined including prostate, heart, brain, and liver. In contrast, p110β is expressed at high levels in brain, heart, kidney and liver, but cannot be readily detected in lymphoid tissues such as spleen. p110β is expressed at high levels in the transformed Jurkat T cell line (Hu et al. 1993). The expression of the p110α isoform has not been well documented.

p110 isoforms have been shown to differ with respect to their preferred substrate specificities [Stephens et al., *Current Biology*, 4:203–214 (1994)]. In view of their potential for interaction with a common p85 adaptor protein, it is likely that the nature of the phosphorylated lipids generated in response to a particular agonist may be regulated at least in part by the cell/tissue specific expression of the different isoforms of the kinase enzymatic activity. The abundant expression of p110δ in PBL and lymphoid tissues such as spleen and thymus suggests that this isoform may be involved in aspects of leukocyte activation.

EXAMPLE 7

Monoclonal antibodies were generated against the carboxy terminal portion of p110δ (amino acids 740–1044 of SEQ ID NO: 2) expressed as a fusion protein with glutathione S transferase (GST) [Pharmacia, Alameda, Calif.]. Five Balb/c mice (Charles River Biotechnical Services, Inc., Wilmington, Mass., IACUC #901103) were immunized subcutaneously with 30 ug of antigen in complete Freund's adjuvant [CFA] (Sigma), a second immunization of 30 ug of antigen in incomplete Freunds adjuvant (IFA) (Sigma) was administered on day 22. A third immunization with 30 ug of antigen in IFA was administered on day 44. Immune serum was collected via retro-orbital bleeding on day 55 and tested by western blotting to determine reactivity to p110δ. All animals showed reactivity towards the immunogen and were immunized a fourth time on day 66 with 30 ug of antigen in IFA. Immune serum was collected via retro-orbital bleeding on day 76 and tested by western blotting to determine its reactivity, animal #2321 showed the highest level of immunoreactivity and was chosen for fusion. On day 367 and 368 mouse #2321 was injected intraperitoneally with 50 ug of antigen in PBS and a fusion was performed on day 371.

The spleen was removed sterilely and a single-cell suspension was formed by grinding the spleen between the frosted ends of two glass microscope slides submerged in serum free RPMI 1640, supplemented with 2 mM L-glutamine, 1mM sodium pyruvate, 100 units/ml penicillin, and 100 μg/ml streptomycin (RPMI) (Gibco, Canada). The cell suspension was filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from 3 naive Balb/c mice were prepared in the same manner.

Two×$10^8$ spleen cells were combined with 4×$10^7$ NS-1 cells (kept in log phase in RPMI with 11% fetal bovine serum (FBS) for three days prior to fusion), centrifuged and the supernatant was aspirated. The cell pellet was dislodged by tapping the tube and 2 ml of 37° C. PEG 1500 (50% in 75 mM Hepes, pH 8.0) (Boehrnger Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×10⁶ thymocytes/ml. The suspension was dispensed into ten 96-well flat bottom tissue culture plates (Corning, United Kingdom) at 200 μl/well. Cells were fed on days 2, 4, and 6 days post-fusion by aspirating 100 μl from each well with an 18 G needle (Becton Dickinson), and adding 100 μl/well plating medium containing 10 U/ml IL-6 and lacking thymocytes.

When cell growth reached 60–80% confluence (day 8–10), culture supernatants were taken from each well and screened for reactivity to p110δ by ELISA. Immulon 4 plates (Dynatech, Cambridge, Mass.) were coated at 4° C. with 50 μl/well with 100 ng/well of p110δ:GST or GST in 50 mM carbonate buffer, pH 9.6. Plates were washed 3× with PBS with 0.05%, Tween 20 (PBST), blocked 30 minutes at 37° C. with 0.5% Fish Skin Gelatin. Plates were washed as described above and 50 μl culture supernatant was added. After incubation at 37° C. for 30 minutes, 50 μl of horseradish peroxidase conjugated goat anti-mouse IgG (fc) (Jackson ImmunoResearch, West Grove, Pa.) [diluted 1:10,000 in PBST] was added. Plates were incubated at 37° C. for 30 minutes, washed 4× with PBST and 100 μl of substrate, consisting of 1 mg/ml TMB (Sigma) and 0.15 ml/ml 30% $H_2O_2$ in 100 mM Citrate, pH 4.5, was added. The color reaction was stopped in 3 minutes with the addition of 50 ml of 15% $H_2SO_4$. $A_{450}$ was read on a plate reader (Dynatech).

Thirty-six wells showed preferential reactivity to p110δ versus GST. Supernatants from these wells were then screened for reactivity to recombinant p110δ by Western blotting. Ten wells (208A, 208B, 208C, 208D, 208E, 208F, 208G, 208H, 208I, and 208J) showed reactivity by Western blotting and were cloned twice by limiting dilution. Selected wells were tested by ELISA 7–10 days later. Activity was retained in all ten lines. Monoclonal antibodies produced by the cell lines were isotyped by ELISA assay. 208A, 208C, 208D, 208E, 208G, 208H, 208I were $IgG_{2a}$, while 208J was $IgG_1$ and 208B was IgG2b. An exemplary monoclonal antibody, produced by hybridoma cell line 208F (ATCC HB 12200), showed high reactivity with p110δ and recognized a 110 kD protein in PBMC by Western analysis. The molecular weight of the 110 kD protein is consistent with the molecular weight of p110δ.

EXAMPLE 8

Elevated levels of 3' phosphorylated phosphoinositides have been detected in cells transformed with viral oncoproteins. This observation suggests that PI 3-kinases may play a role in carcinogenesis. Chromosomal localization of p110δ provides insights into the role of PI 3-kinase in carcinogenesis. Chromosomal localization studies of p110δ of cancerous cells may identify inappropriate and/or over expression of p110δ.

For example, in 90–95% of chronic myelogenous leukaemia there is a reciprocal chromosomal translocation which leads to the transfer of the tyrosine kinase c-abl from chromosome 9 into the ber gene on chromosome 22. The resultant inappropriate expression of c-abl tyrosine kinase activity is critical for cell transformation and tumorigenesis. Chromosomal localization of p110δ is determined by fluorescence in situ hybridization (FISH) using the complete cDNA for p110δ as a probe. In this manner, the role of p110δ in chromosomal translocations observed during tumorigenesis (e.g. leukemogenesis) is identified.

EXAMPLE 9

PI 3-kinase activity has been reported to be associated with a number of growth factor receptors. In addition, it has been observed that PI 3-kinase activity increases following cell activation. The antibodies to p110δ disclosed in Example 5 are utilized to determine by Western blotting and immunoprecipitation the nature of the receptors with which p110δ associates. These antibodies are also useful in elucidating the regulation of PI 3-kinase enzymatic activity and cellular localization during cell activation. In view of the high levels of expression of p110δ in the immune system, it is likely that growth factor receptors involved in immune activation may associate with or be regulated by p110δ. These receptors include T-cell receptors CD28 and CD2 and cytokine receptors such as IL-1 and IL-4, and tyrosine kinase coupled receptors such as CSF-1 R.

EXAMPLE 10

To determine the functional role of p110δ in vivo, the p110δ gene is inactivated in the germline of mammals by homologous recombination. Animals in which an endogenous gene has been inactivated by homologous recombination are also known as "knockout" animals. Exemplary mammals include rabbits and rodent species such as mice. "Knockout" animals can be prepared by homologous recombination methods using the p110δ genomic clone of Example 3.

These "knockout" animals allow for the determination of the role of p110δ in immune and proliferative responses. The role of p110δ in immune and proliferative response is determined by analysis of the development of the immune system in these animals (as determined by FACS analysis of cell populations at different stages of development), characterization of the effector function of the mature lymphoid populations of these animals both in vivo (as determined by antibody responses to injected antigens, cytotoxic T cell responses to viruses and or injected tumor cell lines, and the ability to reject allografts) and in vitro (as determined by proliferation of lymphocytes in response to allo-antigen, polyclonal activation by mitogens/superantigens, and the ability to elaborate cytokines).

While the present invention has been described in terms of specific embodiments, it is understood that variations and modifications will occur to those skilled in the art. Accordingly, only such limitations as appear in the appended claims should be placed on the invention.

What is claimed:

1. A method of identifying a compound that is a modulator of p110δ having SEQ ID NO: 2, comprising the steps of:
 a) determining the kinase activity of p110δ in the absence and presence of the compound;
 b) comparing the kinase activities observed in step (a); and
 c) identifying the compound as a modulator of p110δ wherein a difference in kinase activity is observed in the presence and absence of said compound.

2. A method of identifying a compound that is a modulator of binding between p110δ of SEQ ID NO: 2, and a binding partner comprising the steps of:
 a) determining the level of binding between p110δ and the binding partner in the absence and presence of the compound;
 b) comparing the level of binding observed in step (a); and
 c) identifying the compound as a modulator of the binding between p110δ and the binding partner wherein a difference in binding is observed in the presence and absence of said compound.

3. The method of claim 2 wherein said binding partner is p85.

4. The method of claim 2 wherein said binding partner is Ras.

5. The method of claim 2 wherein said binding partner is a growth factor receptor.

\* \* \* \* \*

SEQUENCE LISTING (1) GENERAL INFORMATION:

(iii) NUMBER OF SEQUENCES: 17

(2) INFORMATION FOR SEQ ID NO:1:

5,985,589

15 16

-continued

```
(i) SEQUENCE CHARACTERISTICS:
    (A) LENGTH: 5220 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 196..3327

(xi) SEQUENCE DESCRIPTION: SEQ ID NO:1:
```

| | | |
|---|---|---|
| CAGTCGCTCC GAGCGGCCGC GAGCAGAGCC GCCCAGCCCT GTCAGCTGCG CCGGGACGAT | | 60 |
| AAGGAGTCAG GCCAGGGCGG GATGACACTC ATTGATTCTA AAGCATCTTT AATCTGCCAG | | 120 |
| GCGGAGGGGG CTTTGCTGGT CTTTCTTGGA CTATTCCAGA GGACAACT GTCATCTGGG | | 180 |

```
AAGTAACAAC GCAGG ATG CCC CCT GGG GTG GAC TGC CCC ATG GAA TTC TGG        231
              Met Pro Pro Gly Val Asp Cys Pro Met Glu Phe Trp
                1               5                  10

ACC AAG GAG GAG AAT CAG AGC GTT GTG GTT GAC TTC CTG CTG CCC ACA         279
Thr Lys Glu Glu Asn Gln Ser Val Val Val Asp Phe Leu Leu Pro Thr
             15                  20                  25

GGG GTC TAC CTG AAC TTC CCT GTG TCC CGC AAT GCC AAC CTC AGC ACC         327
Gly Val Tyr Leu Asn Phe Pro Val Ser Arg Asn Ala Asn Leu Ser Thr
         30                  35                  40

ATC AAG CAG CTG CTG TGG CAC CGC GCC CAG TAT GAG CCG CTC TTC CAC         375
Ile Lys Gln Leu Leu Trp His Arg Ala Gln Tyr Glu Pro Leu Phe His
 45                  50                  55                  60

ATG CTC AGT GGC CCC GAG GCC TAT GTG TTC ACC TGC ATC AAC CAG ACA         423
Met Leu Ser Gly Pro Glu Ala Tyr Val Phe Thr Cys Ile Asn Gln Thr
                 65                  70                  75

GCG GAG CAG CAA GAG CTG GAG GAC GAG CAA CGG CGT CTG TGT GAC GTG         471
Ala Glu Gln Gln Glu Leu Glu Asp Glu Gln Arg Arg Leu Cys Asp Val
             80                  85                  90

CAG CCC TTC CTG CCC GTC CTG CGC CTG GTG GCC CGT GAG GGC GAC CGC         519
Gln Pro Phe Leu Pro Val Leu Arg Leu Val Ala Arg Glu Gly Asp Arg
         95                 100                 105

GTG AAG AAG CTC ATC AAC TCA CAG ATC AGC CTC CTC ATC GGC AAA GGC         567
Val Lys Lys Leu Ile Asn Ser Gln Ile Ser Leu Leu Ile Gly Lys Gly
110                 115                 120

CTC CAC GAG TTT GAC TCC TTG TGC GAC CCA GAA GTG AAC GAC TTT CGC         615
Leu His Glu Phe Asp Ser Leu Cys Asp Pro Glu Val Asn Asp Phe Arg
125                 130                 135                 140

GCC AAG ATG TGC CAA TTC TGC GAG GAG GCG GCC GCC CGC CGG CAG CAG         663
Ala Lys Met Cys Gln Phe Cys Glu Glu Ala Ala Ala Arg Arg Gln Gln
                145                 150                 155

CTG GGC TGG GAG GCC TGG CTG CAG TAC AGT TTC CCC CTG CAG CTG GAG         711
Leu Gly Trp Glu Ala Trp Leu Gln Tyr Ser Phe Pro Leu Gln Leu Glu
            160                 165                 170

CCC TCG GCT CAA ACC TGG GGG CCT GGT ACC CTG CGG CTC CCG AAC CGG         759
Pro Ser Ala Gln Thr Trp Gly Pro Gly Thr Leu Arg Leu Pro Asn Arg
        175                 180                 185

GCC CTT CTG GTC AAC GTT AAG TTT GAG GGC AGC GAG GAG AGC TTC ACC         807
Ala Leu Leu Val Asn Val Lys Phe Glu Gly Ser Glu Glu Ser Phe Thr
    190                 195                 200

TTC CAG GTG TCC ACC AAG GAC GTG CCG CTG GCG CTG ATG GCC TGT GCC         855
Phe Gln Val Ser Thr Lys Asp Val Pro Leu Ala Leu Met Ala Cys Ala
205                 210                 215                 220

CTG CGG AAG AAG GCC ACA GTG TTC CGG CAG CCG CTG GTG GAG CAG CCG         903
Leu Arg Lys Lys Ala Thr Val Phe Arg Gln Pro Leu Val Glu Gln Pro
                225                 230                 235
```

```
GAA GAC TAC ACG CTG CAG GTG AAC GGC AGG CAT GAG TAC CTG TAT GGC      951
Glu Asp Tyr Thr Leu Gln Val Asn Gly Arg His Glu Tyr Leu Tyr Gly
            240                 245                 250

AAC TAC CCG CTC TGC CAG TTC CAG TAC ATC TGC AGC TGC CTG CAC AGT      999
Asn Tyr Pro Leu Cys Gln Phe Gln Tyr Ile Cys Ser Cys Leu His Ser
                255                 260                 265

GGG TTG ACC CCT CAC CTG ACC ATG GTC CAT TCC TCC TCC ATC CTC GCC     1047
Gly Leu Thr Pro His Leu Thr Met Val His Ser Ser Ser Ile Leu Ala
270                 275                 280

ATG CGG GAT GAG CAG AGC AAC CCT GCC CCC CAG GTC CAG AAA CCG CGT     1095
Met Arg Asp Glu Gln Ser Asn Pro Ala Pro Gln Val Gln Lys Pro Arg
285                 290                 295                 300

GCC AAA CCA CCT CCC ATT CCT GCG AAG AAG CCT TCC TCT GTG TCC CTG     1143
Ala Lys Pro Pro Pro Ile Pro Ala Lys Lys Pro Ser Ser Val Ser Leu
                305                 310                 315

TGG TCC CTG GAG CAG CCG TTC CGC ATC GAG CTC ATC CAG GGC AGC AAA     1191
Trp Ser Leu Glu Gln Pro Phe Arg Ile Glu Leu Ile Gln Gly Ser Lys
                320                 325                 330

GTG AAC GCC GAC GAG CGG ATG AAG CTG GTG GTG CAG GCC GGG CTT TTC     1239
Val Asn Ala Asp Glu Arg Met Lys Leu Val Val Gln Ala Gly Leu Phe
            335                 340                 345

CAC GGC AAC GAG ATG CTG TGC AAG ACG GTG TCC AGC TCG GAG GTG AGC     1287
His Gly Asn Glu Met Leu Cys Lys Thr Val Ser Ser Ser Glu Val Ser
            350                 355                 360

GTG TGC TCG GAG CCC GTG TGG AAG CAG CGG CTG GAG TTC GAC ATC AAC     1335
Val Cys Ser Glu Pro Val Trp Lys Gln Arg Leu Glu Phe Asp Ile Asn
365                 370                 375                 380

ATC TGC GAC CTG CCC CGC ATG GCC CGT CTC TGC TTT GCG CTG TAC GCC     1383
Ile Cys Asp Leu Pro Arg Met Ala Arg Leu Cys Phe Ala Leu Tyr Ala
                385                 390                 395

GTG ATC GAG AAA GCC AAG AAG GCT CGC TCC ACC AAG AAG AAG TCC AAG     1431
Val Ile Glu Lys Ala Lys Lys Ala Arg Ser Thr Lys Lys Lys Ser Lys
                400                 405                 410

AAG GCG GAC TGC CCC ATT GCC TGG GCC AAC CTC ATG CTG TTT GAC TAC     1479
Lys Ala Asp Cys Pro Ile Ala Trp Ala Asn Leu Met Leu Phe Asp Tyr
            415                 420                 425

AAG GAC CAG CTT AAG ACC GGG GAA CGC TGC CTC TAC ATG TGG CCC TCC     1527
Lys Asp Gln Leu Lys Thr Gly Glu Arg Cys Leu Tyr Met Trp Pro Ser
            430                 435                 440

GTC CCA GAT GAG AAG GGC GAG CTG CTG AAC CCC ACG GGC ACT GTG CGC     1575
Val Pro Asp Glu Lys Gly Glu Leu Leu Asn Pro Thr Gly Thr Val Arg
445                 450                 455                 460

AGT AAC CCC AAC ACG GAT AGC GCC GCT GCC CTG CTC ATC TGC CTG CCC     1623
Ser Asn Pro Asn Thr Asp Ser Ala Ala Ala Leu Leu Ile Cys Leu Pro
                465                 470                 475

GAG GTG GCC CCG CAC CCC GTG TAC TAC CCC GCC CTG GAG AAG ATC TTG     1671
Glu Val Ala Pro His Pro Val Tyr Tyr Pro Ala Leu Glu Lys Ile Leu
            480                 485                 490

GAG CTG GGG CGA CAC AGC GAG TGT GTG CAT GTC ACC GAG GAG GAG CAG     1719
Glu Leu Gly Arg His Ser Glu Cys Val His Val Thr Glu Glu Glu Gln
            495                 500                 505

CTG CAG CTG CGG GAA ATC CTG GAG CGG CGG GGG TCT GGG GAG CTG TAT     1767
Leu Gln Leu Arg Glu Ile Leu Glu Arg Arg Gly Ser Gly Glu Leu Tyr
        510                 515                 520

GAG CAC GAG AAG GAC CTG GTG TGG AAG CTG CGG CAT GAA GTC CAG GAG     1815
Glu His Glu Lys Asp Leu Val Trp Lys Leu Arg His Glu Val Gln Glu
525                 530                 535                 540

CAC TTC CCG GAG GCG CTA GCC CGG CTG CTG CTG GTC ACC AAG TGG AAC     1863
His Phe Pro Glu Ala Leu Ala Arg Leu Leu Leu Val Thr Lys Trp Asn
                545                 550                 555
```

```
AAG CAT GAG GAT GTG GCC CAG ATG CTC TAC CTG CTG TGC TCC TGG CCG      1911
Lys His Glu Asp Val Ala Gln Met Leu Tyr Leu Leu Cys Ser Trp Pro
            560                 565                 570

GAG CTG CCC GTC CTG AGC GCC CTG GAG CTG CTA GAC TTC AGC TTC CCC      1959
Glu Leu Pro Val Leu Ser Ala Leu Glu Leu Leu Asp Phe Ser Phe Pro
            575                 580                 585

GAT TGC CAC GTA GGC TCC TTC GCC ATC AAG TCG CTG CGG AAA CTG ACG      2007
Asp Cys His Val Gly Ser Phe Ala Ile Lys Ser Leu Arg Lys Leu Thr
            590                 595                 600

GAC GAT GAG CTG TTC CAG TAC CTG CTG CAG CTG GTG CAG GTC CTC AAG      2055
Asp Asp Glu Leu Phe Gln Tyr Leu Leu Gln Leu Val Gln Val Leu Lys
605                 610                 615                 620

TAC GAG TCC TAC CTG GAC TGC GAG CTG ACC AAA TTC CTG CTG GAC CGG      2103
Tyr Glu Ser Tyr Leu Asp Cys Glu Leu Thr Lys Phe Leu Leu Asp Arg
            625                 630                 635

GCC CTG GCC AAC CGC AAG ATC GGC CAC TTC CTT TTC TGG CAC CTC CGC      2151
Ala Leu Ala Asn Arg Lys Ile Gly His Phe Leu Phe Trp His Leu Arg
            640                 645                 650

TCC GAG ATG CAC GTG CCG TCG GTG GCC CTG CGC TTC GGC CTC ATC CTG      2199
Ser Glu Met His Val Pro Ser Val Ala Leu Arg Phe Gly Leu Ile Leu
            655                 660                 665

GAG GCC TAC TGC AGG GGC AGC ACC CAC CAC ATG AAG GTG CTG ATG AAG      2247
Glu Ala Tyr Cys Arg Gly Ser Thr His His Met Lys Val Leu Met Lys
            670                 675                 680

CAG GGG GAA GCA CTG AGC AAA CTG AAG GCC CTG AAT GAC TTC GTC AAG      2295
Gln Gly Glu Ala Leu Ser Lys Leu Lys Ala Leu Asn Asp Phe Val Lys
685                 690                 695                 700

CTG AGC TCT CAG AAG ACC CCC AAG CCC CAG ACC AAG GAG CTG ATG CAC      2343
Leu Ser Ser Gln Lys Thr Pro Lys Pro Gln Thr Lys Glu Leu Met His
            705                 710                 715

TTG TGC ATG CGG CAG GAG GCC TAC CTA GAG GCC CTC TCC CAC CTG CAG      2391
Leu Cys Met Arg Gln Glu Ala Tyr Leu Glu Ala Leu Ser His Leu Gln
            720                 725                 730

TCC CCA CTC GAC CCC AGC ACC CTG CTG GCT GAA GTC TGC GTG GAG CAG      2439
Ser Pro Leu Asp Pro Ser Thr Leu Leu Ala Glu Val Cys Val Glu Gln
            735                 740                 745

TGC ACC TTC ATG GAC TCC AAG ATG AAG CCC CTG TGG ATC ATG TAC AGC      2487
Cys Thr Phe Met Asp Ser Lys Met Lys Pro Leu Trp Ile Met Tyr Ser
750                 755                 760

AAC GAG GAG GCA GGC AGC GGC GGC AGC GTG GGC ATC ATC TTT AAG AAC      2535
Asn Glu Glu Ala Gly Ser Gly Gly Ser Val Gly Ile Ile Phe Lys Asn
765                 770                 775                 780

GGG GAT GAC CTC CGG CAG GAC ATG CTG ACC CTG CAG ATG ATC CAG CTC      2583
Gly Asp Asp Leu Arg Gln Asp Met Leu Thr Leu Gln Met Ile Gln Leu
            785                 790                 795

ATG GAC GTC CTG TGG AAG CAG GAG GGG CTG GAC CTG AGG ATG ACC CCC      2631
Met Asp Val Leu Trp Lys Gln Glu Gly Leu Asp Leu Arg Met Thr Pro
            800                 805                 810

TAT GGC TGC CTC CCC ACC GGG GAC CGC ACA GGC CTC ATT GAG GTG GTA      2679
Tyr Gly Cys Leu Pro Thr Gly Asp Arg Thr Gly Leu Ile Glu Val Val
            815                 820                 825

CTC CGT TCA GAC ACC ATC GCC AAC ATC CAA CTC AAC AAG AGC AAC ATG      2727
Leu Arg Ser Asp Thr Ile Ala Asn Ile Gln Leu Asn Lys Ser Asn Met
            830                 835                 840

GCA GCC ACA GCC GCC TTC AAC AAG GAT GCC CTG CTC AAC TGG CTG AAG      2775
Ala Ala Thr Ala Ala Phe Asn Lys Asp Ala Leu Leu Asn Trp Leu Lys
845                 850                 855                 860

TCC AAG AAC CCG GGG GAG GCC CTG GAT CGA GCC ATT GAG GAG TTC ACC      2823
Ser Lys Asn Pro Gly Glu Ala Leu Asp Arg Ala Ile Glu Glu Phe Thr
            865                 870                 875
```

| | |
|---|---|
| CTC TCC TGT GCT GGC TAT TGT GTG GCC ACA TAT GTG CTG GGC ATT GGC<br>Leu Ser Cys Ala Gly Tyr Cys Val Ala Thr Tyr Val Leu Gly Ile Gly<br>880 885 890 | 2871 |
| GAT CGG CAC AGC GAC AAC ATC ATG ATC CGA GAG AGT GGG CAG CTG TTC<br>Asp Arg His Ser Asp Asn Ile Met Ile Arg Glu Ser Gly Gln Leu Phe<br>895 900 905 | 2919 |
| CAC ATT GAT TTT GGC CAC TTT CTG GGG AAT TTC AAG ACC AAG TTT GGA<br>His Ile Asp Phe Gly His Phe Leu Gly Asn Phe Lys Thr Lys Phe Gly<br>910 915 920 | 2967 |
| ATC AAC CGC GAG CGT GTC CCA TTC ATC CTC ACC TAT GAC TTT GTC CAT<br>Ile Asn Arg Glu Arg Val Pro Phe Ile Leu Thr Tyr Asp Phe Val His<br>925 930 935 940 | 3015 |
| GTG ATT CAG CAG GGG AAG ACT AAT AAT AGT GAG AAA TTT GAA CGG TTC<br>Val Ile Gln Gln Gly Lys Thr Asn Asn Ser Glu Lys Phe Glu Arg Phe<br>945 950 955 | 3063 |
| CGG GGC TAC TGT GAA AGG GCC TAC ACC ATC CTG CGG CGC CAC GGG CTT<br>Arg Gly Tyr Cys Glu Arg Ala Tyr Thr Ile Leu Arg Arg His Gly Leu<br>960 965 970 | 3111 |
| CTC TTC CTC CAC CTC TTT GCC CTG ATG CGG GCG GCA GGC CTG CCT GAG<br>Leu Phe Leu His Leu Phe Ala Leu Met Arg Ala Ala Gly Leu Pro Glu<br>975 980 985 | 3159 |
| CTC AGC TGC TCC AAA GAC ATC CAG TAT CTC AAG GAC TCC CTG GCA CTG<br>Leu Ser Cys Ser Lys Asp Ile Gln Tyr Leu Lys Asp Ser Leu Ala Leu<br>990 995 1000 | 3207 |
| GGG AAA ACA GAG GAG GAG GCA CTG AAG CAC TTC CGA GTG AAG TTT AAC<br>Gly Lys Thr Glu Glu Glu Ala Leu Lys His Phe Arg Val Lys Phe Asn<br>1005 1010 1015 1020 | 3255 |
| GAA GCC CTC CGT GAG AGC TGG AAA ACC AAA GTG AAC TGG CTG GCC CAC<br>Glu Ala Leu Arg Glu Ser Trp Lys Thr Lys Val Asn Trp Leu Ala His<br>1025 1030 1035 | 3303 |
| AAC GTG TCC AAA GAC AAC AGG CAG TAGTGGCTCC TCCCAGCCCT GGGCCCAAGA<br>Asn Val Ser Lys Asp Asn Arg Gln<br>1040 | 3357 |
| GGAGGCGGCT GCGGGTCGTG GGACCAAGC ACATTGGTCC TAAAGGGGCT GAAGAGCCTG | 3417 |
| AACTGCACCT AACGGGAAAG AACCGACATG GCTGCCTTTT GTTTACACTG GTTATTTATT | 3477 |
| TATGACTTGA AATAGTTTAA GGAGCTAAAC AGCCATAAAC GGAAACGCCT CCTTCATTCA | 3537 |
| GCGGCGGTGC TGGGCCCCCC GAGGCTGCAC CTGGCTCTCG GCTGAGGATT GTCACCCCAA | 3597 |
| GTCTTCCAGC TGGTGGATCT GGGCCCAGCA AAGACTGTTC TCCTCCCGAG GGAACCTTCT | 3657 |
| TCCCAGGCCT CCCGCCAGAC TGCCTGGGTC CTGGCGCCTG GCGGTCACCT GGTGCCTACT | 3717 |
| GTCCGACAGG ATGCCTCGAT CCTCGTGCGA CCCACCCTGT GTATCCTCCC TAGACTGAGT | 3777 |
| TCTGGCAGCT CCCCGAGGCA GCCGGGGTAC CCTCTAGATT CAGGGATGCT TGCTCTCCAC | 3837 |
| TTTTCAAGTG GGTCTTGGGT ACGAGAATTC CCTCATCTTT CTCTACTGTA AAGTGATTTT | 3897 |
| GTTTGCAGGT AAGAAAATAA TAGATGACTC ACCACACCTC TACGGCTGGG GAGATCAGGC | 3957 |
| CCAGCCCCAT AAAGGAGAAT CTACGCTGGT CCTCAGGACG TGTTAAAGAG ATCTGGGCCT | 4017 |
| CATGTAGCTC ACCCCGGTCA CGCATGAAGG CAAAAGCAGG TCAGAAGCGA ATACTCTGCC | 4077 |
| ATTATCTCAA AAATCTTTTT TTTTTTTTTT TTGAGATGGG GTCTTCCTCT GTTGCCCAGG | 4137 |
| CTGGAGTGCA GTGGTGCAAT CTTGGCTCAC TGTAACCTCC GCCTCCCAGG TTCAAGTGAT | 4197 |
| TCTTCTTGCC TCAGCCTCCT GAGTAGCTGG GATTACAGGT GTGCACCACC CGTACCCAGC | 4257 |
| TAATTTTTGT ATTTTAGTAG AGACGGGGGT TTCACCATGT TGGCTGGGCT GGTCTCGAAC | 4317 |
| TCCTGACCTC AGGTGATCCA CCCGCCTGAG CCTCCCAAAG TGCTGGGATT ACAGGCATGA | 4377 |
| GCCACCACGC CCGGCCCACT CTGCCATTGT CTAAGCCACC TCTGAAAGCA GGTTTTAACA | 4437 |

```
AAAGGATGAG GCCAGAACTC TTCCAGAACC ATCACCTTTG GGAACCTGCT GTGAGAGTGC    4497

TGAGGTACCA GAAGTGTGAG AACGAGGGGG CGTGCTGGGA TCTTTCTCTC TGACTATACT    4557

TAGTTTGAAA TGGTGCAGGC TTAGTCTTAA GCCTCCAAAG GCCTGGATTT GAGCAGCTTT    4617

AGAAATGCAG GTTCTAGGGC TTCTCCCAGC CTTCAGAAGC CAACTAACTC TGCAGATGGG    4677

GCTAGGACTG TGGGCTTTTA GCAGCCCACA GGTGATCCTA ACATATCAGG CCATGGACTC    4737

AGGACCTGCC CGGTGATGCT GTTGATTTCT CAAAGGTCTT CCAAAACTCA ACAGAGCCAG    4797

AAGTAGCCGC CCGCTCAGCG GCTCAGGTGC CAGCTCTGTT CTGATTCACC AGGGGTCCGT    4857

CAGTAGTCAT TGCCACCCGC GGGGCACCTC CCTGGCCACA CGCCTGTTCC CAGCAAGTGC    4917

TGAAACTCAC TAGACCGTCT GCCTGTTTCG AAATGGGGAA AGCCGTGCGT GCGCGTTATT    4977

TATTTAAGTG CGCCTGTGTG CGCGGGTGTG GGAGCACACT TTGCAAAGCC ACAGCGTTTC    5037

TGGTTTTGGG TGTACAGTCT TGTGTGCCTG GCGAGAAGAA TATTTTCTAT TTTTTTAAGT    5097

CATTTCATGT TTCTGTCTGG GGAAGGCAAG TTAGTTAAGT ATCACTGATG TGGGTTGAGA    5157

CCAGCACTCT GTGAAACCTT GAAATGAGAA GTAAAGGCAG ATGAAAAGAA AAAAAAAAA    5217

AAA                                                                 5220

(2) INFORMATION FOR SEQ ID NO:2:

(i) SEQUENCE CHARACTERISTICS:
        (A) LENGTH: 1044 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Pro Gly Val Asp Cys Pro Met Glu Phe Trp Thr Lys Glu Glu
 1               5                  10                  15

Asn Gln Ser Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205
```

-continued

Thr Lys Asp Val Pro Leu Ala Leu Met Ala Cys Ala Leu Arg Lys Lys
210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Asn Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ile Leu Ala Met Arg Asp Glu
        275                 280                 285

Gln Ser Asn Pro Ala Pro Gln Val Gln Lys Pro Arg Ala Lys Pro Pro
290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Glu Val Ser Val Cys Ser Glu
        355                 360                 365

Pro Val Trp Lys Gln Arg Leu Glu Phe Asp Ile Asn Ile Cys Asp Leu
370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Ser Lys Lys Ala Asp Cys
                405                 410                 415

Pro Ile Ala Trp Ala Asn Leu Met Leu Phe Asp Tyr Lys Asp Gln Leu
            420                 425                 430

Lys Thr Gly Glu Arg Cys Leu Tyr Met Trp Pro Ser Val Pro Asp Glu
        435                 440                 445

Lys Gly Glu Leu Leu Asn Pro Thr Gly Thr Val Arg Ser Asn Pro Asn
450                 455                 460

Thr Asp Ser Ala Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Gln Leu Gln Leu Arg
            500                 505                 510

Glu Ile Leu Glu Arg Arg Gly Ser Gly Glu Leu Tyr Glu His Glu Lys
        515                 520                 525

Asp Leu Val Trp Lys Leu Arg His Glu Val Gln Glu His Phe Pro Glu
530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
            580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
610                 615                 620

Leu Asp Cys Glu Leu Thr Lys Phe Leu Leu Asp Arg Ala Leu Ala Asn
625                 630                 635                 640

```
Arg Lys Ile Gly His Phe Leu Phe Trp His Leu Arg Ser Glu Met His
            645                 650                 655

Val Pro Ser Val Ala Leu Arg Phe Gly Leu Ile Leu Glu Ala Tyr Cys
            660                 665                 670

Arg Gly Ser Thr His His Met Lys Val Leu Met Lys Gln Gly Glu Ala
            675                 680                 685

Leu Ser Lys Leu Lys Ala Leu Asn Asp Phe Val Lys Leu Ser Ser Gln
            690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
            725                 730                 735

Pro Ser Thr Leu Leu Ala Glu Val Cys Val Glu Gln Cys Thr Phe Met
            740                 745                 750

Asp Ser Lys Met Lys Pro Leu Trp Ile Met Tyr Ser Asn Glu Glu Ala
            755                 760                 765

Gly Ser Gly Gly Ser Val Gly Ile Ile Phe Lys Asn Gly Asp Asp Leu
            770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
            805                 810                 815

Pro Thr Gly Asp Arg Thr Gly Leu Ile Glu Val Val Leu Arg Ser Asp
            820                 825                 830

Thr Ile Ala Asn Ile Gln Leu Asn Lys Ser Asn Met Ala Ala Thr Ala
            835                 840                 845

Ala Phe Asn Lys Asp Ala Leu Leu Asn Trp Leu Lys Ser Lys Asn Pro
850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
            885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
            915                 920                 925

Arg Val Pro Phe Ile Leu Thr Tyr Asp Phe Val His Val Ile Gln Gln
            930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
            965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp Ser Leu Ala Leu Gly Lys Thr Glu
            995                 1000                1005

Glu Glu Ala Leu Lys His Phe Arg Val Lys Phe Asn Glu Ala Leu Arg
    1010                1015                1020

Glu Ser Trp Lys Thr Lys Val Asn Trp Leu Ala His Asn Val Ser Lys
1025                1030                1035                1040

Asp Asn Arg Gln
```

(2) INFORMATION FOR SEQ ID NO:3:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: misc_feature
            (B) LOCATION: 15
            (D) OTHER INFORMATION: /note= "n=inosine"

(ix) FEATURE:
            (A) NAME/KEY: misc_feature
            (B) LOCATION: 24
            (D) OTHER INFORMATION: /note= "n=inosine"

(xi) SEQUENCE DESCRIPTION: SEQ ID NO:3:

GCAGACGGAT CCGGNGAYGA YHKNAGRCAR GA                                          32

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:4:

Gly Asp Asp Leu Arg Gln Asp
1               5

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: misc_feature
            (B) LOCATION: 16
            (D) OTHER INFORMATION: /note= "n = inosine"

(ix) FEATURE:
            (A) NAME/KEY: misc_feature
            (B) LOCATION: 25
            (D) OTHER INFORMATION: /note= "n=inosine"

(xi) SEQUENCE DESCRIPTION: SEQ ID NO:5:

GCAGACGAAT TCRWRNCCRA ARTCNRYRTG                                             30

(2) INFORMATION FOR SEQ ID NO:6:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:6:

His Ile Asp Phe Gly His
1               5

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

```
CATGCTGACC CTGCAGATGA T                                              21
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
AACAGCTGCC CACTCTCTCG G                                              21
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGGCCACATG TAGAGGCAGC GTTCCC                                         26
```

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GGCCCAGGCA ATGGGGCAGT CCGCC                                          25
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

```
GATGCGGAAC GGCTGCTCCA GGG                                            23
```

(2) INFORMATION FOR SEQ ID NO:12:

(i) SEQUENCE CHARACTERISTICS:
        (A) LENGTH: 23 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CCAGGGACCA CAGGGACACA GAG                                         23

(2) INFORMATION FOR SEQ ID NO:13:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

AGTTACGGAT CCGGCACCAT GGACTACAAG GACGACGATG ACAAGCCCCC TGGGGTGGAC    60

TGCCC                                                             65

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

CCACATGTAG AGGCAGCGTT CC                                          22

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

Asp Tyr Lys Asp Asp Asp Asp Lys
1               5

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CTGCCATGTT GCTCTTGTTG A                                           21

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single

```
      (D) TOPOLOGY: linear (ii) MOLECULE TYPE: other nucleic acid (xi) SEQUENCE DESCRIPTION: SEQ ID NO:17:

GAGTTCGACA TCAACATC                                                    18
```